United States Patent
Nishtala

(10) Patent No.: US 8,403,884 B2
(45) Date of Patent: Mar. 26, 2013

(54) ACS THERAPY SYSTEM

(75) Inventor: Vasu Nishtala, Snellville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 806 days.

(21) Appl. No.: 12/527,985

(22) PCT Filed: Feb. 18, 2008

(86) PCT No.: PCT/US2008/054199
§ 371 (c)(1),
(2), (4) Date: Aug. 20, 2009

(87) PCT Pub. No.: WO2008/103625
PCT Pub. Date: Aug. 28, 2008

(65) Prior Publication Data
US 2010/0094204 A1    Apr. 15, 2010

Related U.S. Application Data

(60) Provisional application No. 60/890,853, filed on Feb. 21, 2007.

(51) Int. Cl.
A61M 31/00 (2006.01)
A61M 1/00 (2006.01)
A61M 27/00 (2006.01)
A61B 5/00 (2006.01)

(52) U.S. Cl. ....... 604/93.01; 604/118; 604/66; 604/540; 604/544; 600/561

(58) Field of Classification Search .............. 604/33, 604/77, 93.01, 167.04, 167.03, 248, 339, 604/39, 45, 540, 544, 66, 118; 600/561, 600/591

See application file for complete search history.

(56) References Cited

U.S. PATENT DOCUMENTS

| 4,343,316 | A | 8/1982 | Jespersen |
| 5,078,688 | A | 1/1992 | Lobodzinski et al. |
| 5,433,216 | A | 7/1995 | Sugrue et al. |
| 5,938,626 | A | 8/1999 | Sugerman |
| 6,497,676 | B1 * | 12/2002 | Childers et al. .................. 604/29 |
| 8,052,671 | B2 * | 11/2011 | Christensen et al. ......... 604/540 |
| 2006/0058702 | A1 | 3/2006 | Christensen et al. |

(Continued)

FOREIGN PATENT DOCUMENTS

| WO | WO 2006041496 | * | 4/2006 |
| WO | 2007018963 A2 | | 2/2007 |
| WO | 2008103625 A2 | | 8/2008 |

OTHER PUBLICATIONS

Parra et al., Journal of Trauma—Injury Infection & Critical Care: May 2006—vol. 60—Issue 5—pp. 1119-1121.*

(Continued)

*Primary Examiner* — Matthew F Desanto
(74) *Attorney, Agent, or Firm* — Rutan & Tucker, LLP

(57) ABSTRACT

An ACS therapy system for continuously monitoring Intra-Abdominal Pressure (IAP) and preventing the onset of ACS. The automated ACS therapy system includes a urine withdrawal device, an IAP regulation circuit, an IAP monitor connected to the urine withdrawal device to supply an IAP value to the IAP regulation circuit, and an abdominal fluid removal device. The abdominal fluid removal device may be connected to an active suction device, which withdraws fluid from the abdominal cavity through the abdominal fluid removal device when activated by the IAP regulation circuit. Based on the IAP value, the IAP regulation circuit may send a control signal that controls the active suction device to turn on and drain fluid from the abdominal cavity. When the IAP value reaches certain levels, the IAP regulation circuit may cause the active suction device to be turned off.

20 Claims, 5 Drawing Sheets

U.S. PATENT DOCUMENTS

2006/0129136 A1* 6/2006 Meacham .................. 604/540
2006/0270971 A1* 11/2006 Gelfand et al. ............... 604/66

OTHER PUBLICATIONS

KCI® Vacuum Assisted Closure (V.A.C.®) ATS âSystem described at http://www.kci1.com/KCI1/vactherapy, last accessed Dec. 27, 2011.

PCT/US2008/054199 filed Feb. 18, 2008 International Preliminary Report on Patentability dated Aug. 26, 2009.

PCT/US2008/054199 filed Feb. 18, 2008 Search Report dated Aug. 8, 2008.

PCT/US2008/054199 filed Feb. 18, 2008 Written Opinion dated Aug. 8, 2008.

* cited by examiner

ACS THERAPY SYSTEM

This application is a U.S. national stage application under 35 USC §371 of International Application No PCT/US2008/054199, filed Feb. 18, 2008, claiming priority to U.S. Provisional Patent Application No. 60/890,853, filed Feb. 21, 2007, the disclosures of which are incorporated herein by reference in their entirety.

BACKGROUND OF THE INVENTION

Fluid resuscitation, which involves the administration of as much as 12 liters of fluid in a 24-hour period, often through an IntraVenous (IV) catheter, is employed to maintain blood pressure, avoid collapsing of blood vessels, and maintain systemic vascular function in trauma patients suffering from exposed and ruptured blood vessels. Normally, this fluid is removed from the body in the form of urine, often through a Foley catheter. To stabilize the balance of fluid being provided to the body and urine being drained from the body, diuretics may be given to the patient to stimulate urination. This process of both providing fluid to the body and removing urine from the body can be characterized as a gross intervention.

However, trauma patients often have difficulty urinating, and may suffer from oliguria (secretion of a diminished amount of urine in relation to fluid intake) or anuria (complete suppression of urine secretion by the kidneys). Even non-trauma patients whose kidneys have shut down due to the effects of anesthesia at other causes can suffer from oliguria or anuria. If excess fluid builds up in the body due to the lack of urine production, it tends to escape from tissues and linings of the cells into the abdominal cavity. As this fluid fills the interstitial spaces in the abdominal cavity, elevated Intra-Abdominal Pressure (IAP) in the abdominal cavity, referred to as Intra-Abdominal Hypertension (IAH), can cause bloating of the cavity and pressure on other vital organs in the abdominal cavity. This increased pressure can cause a restriction of the blood vessels and blood supply to those organs, leading to organ dysfunction and failure, a condition referred to as Abdominal Compartment Syndrome (ACS). Other causes of IAH and ACS include intraperitoneal blood, peritonitis, ascites, and gaseous bowel distention. Primary organ systems adversely affected by IAH and ACS include the cardiovascular, renal, pulmonary, gastrointestinal, and central nervous systems.

Because the effectiveness of diuretics and the amount of urine produced by the patient can vary, fluid resuscitation requires a delicate and precise balance of fluid input and output, with some form of monitoring to manage the patient and ensure that the proper amount of fluid is being administered given the effectiveness of the diuretic and the amount of urine being produced. IAP can therefore be an important diagnostic and prognostic indicator of a patient's underlying physiologic status. A high reading may be an indication that a laparotomy (abdominal surgery) may be necessary to open the abdominal cavity and relieve the pressure. Correct IAP measurement is therefore crucial.

Several techniques for measuring IAP have been described in the literature. One simple way of indirectly detecting and measuring IAP is the measurement of bladder pressure via an indwelling urinary catheter system. The bladder acts as a passive reservoir and accurately reflects intra-abdominal pressure when the intravesicular volume is approximately 100 mL or less. Because bladder pressure can be easily and reliably measured by using a conventional pressure transducer or monitor connected to the patient's urinary catheter drainage system, measurement of bladder pressure has become the method of choice.

Serial measurements of bladder pressure should be undertaken as part of the examination of any patient at risk for IAH or ACS, and the measurement of IAP should be correlated with other assessment findings associated with organ system compromise. However, most bladder pressure measurements are manually performed by medical professions on an ad-hoc basis, and are taken less frequently than would be beneficial. Moreover, although elevated IAP may be an indication of kidney malfunction, currently there are no systems that utilize IAP measurements to manage and prevent ACS.

Thus, there is a need to obtain continuous measurements of IAP and optionally other parameters, and provide continuous and automatic therapy in an active feedback system in response to those parameters to prevent the onset of IAH and ACS.

BRIEF SUMMARY OF THE INVENTION

Accordingly, an ACS therapy system is described herein for continuously managing fluid resuscitation and automatically intervening on behalf of a patient to provide ACS therapy using minimally-invasive techniques. The automated ACS therapy system fundamentally includes an IAP regulation circuit, an Intra-Abdominal Pressure (IAP) monitor connected to the urine withdrawal device to supply an IAP value representative of the pressure in the abdominal cavity to the IAP regulation circuit, and an abdominal fluid removal device to withdraw fluid from the abdominal cavity under control of the IAP regulation circuit. The abdominal fluid removal device may be connected to an active suction device, which withdraws fluid from the abdominal cavity through the abdominal fluid removal device when activated by the IAP regulation circuit, and may provide an abdominal fluid volume value to the IAP regulation circuit. The ACS therapy system may also include a urine withdrawal device to withdraw urine from the bladder and a urine output monitor that receives urine through the urine withdrawal device, measures total urine output, and provides this value to the IAP regulation circuit.

During fluid resuscitation, an IntraVenous (IV) catheter may be used to administer fluid to the body. The catheter is connected to a fluid delivery source and is inserted into the body. The ACS therapy system may also include a fluid control and monitoring device to control and monitor the amount of fluid being delivered to the body, and provide a fluid volume value to the IAP regulation circuit. The IV catheter may also be connected to a diuretic delivery source and used to administer diuretics to the body. The ACS therapy system may also include a diuretic control and monitoring device to control and monitor the amount of diuretics being delivered to the body, and provide a diuretic volume value to the IAP regulation circuit.

The ACS therapy system is an active feedback system. Based on one or more of the total urine output, the IAP value, the abdominal fluid volume value, the fluid volume value and the diuretic volume value, the IAP regulation circuit may send a control signal that controls the active suction device. For example, if the IAP value indicates that the intra-abdominal pressure is too great, the IAP regulation circuit may cause the active suction device to turn on and drain fluid from the abdominal cavity. When the IAP value and/or the amount of fluid drained from the abdominal cavity reach certain levels as determined by the abdominal fluid volume value, or a certain amount of time has elapsed, the IAP regulation circuit may cause the active suction device to be turned off, causing the draining of fluid from the abdominal cavity to cease.

The IAP monitor may include an inflatable element that is expanded inside a patient's bladder. The resistance felt by the balloon when making contact with the bladder wall is detected through an inflation lumen via a pressure transducer or sensor, which may be located within the IAP monitor.

The abdominal fluid removal device may be a Peritoneal Dialysis (PD) catheter. The PD catheter is a length of tubing with holes in its sides that is placed within the abdominal cavity through a small incision. The PD catheter is used to pull excess fluid from the abdominal cavity when the active suction device is activated.

The fluid delivery source provides fluids to the body through the IV catheter. Feedback (monitoring information) received by the IAP regulation circuit may enable the IAP regulation circuit to determine that a different type of IV fluid should be delivered to the body through the IV catheter. For example, if the IAP regulation circuit determines indicates that a large amount of fluid is being removed from the abdominal cavity, or that some other complication capable of being detected by the parameters monitored by the IAP regulation circuit is occurring, it may provide an visual or audio indication that a different type of IV fluid should be used, or the IV fluid should be applied at a slower rate. Alternatively, the IAP regulation circuit may provide a control signal to a fluid switch to automatically change fluids or rates of delivery.

The IAP regulation circuit may include A/D converters for receiving one or more analog inputs, an elapsed time signal from a clock circuit, a processor for receiving the inputs and controlling the components of the ACS therapy system, and a user interface for enabling a user to establish a start time so that total elapsed time can be determined, and for enabling the user to input parameters and programming information. A number of algorithms may be implemented by the IAP regulation circuit to monitor IAP, the fluid and the diuretics being administered, and control the withdrawal of fluid from the abdominal cavity, or control the amount or type of fluid or diuretics being administered. The IAP regulation circuit may also include a continuous printing device or graphical display and memory for printing out and/or displaying and storing any one or more of the parameters being monitored and computed on a continuous basis to show one or more of the changes in IAP, urine output, abdominal fluid removal, fluid and diuretics being administered, and the relationship between them, over time.

These and other embodiments, methods, features and advantages will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Embodiments described herein relate generally to a continuous ACS therapy system that manages and balances the gross intervention of fluid resuscitation and automatically intervenes on behalf of a patient to provide ACS therapy using minimally-invasive techniques. Embodiments described herein are believed to be advantageous compared to other gross interventions, such as, for example, making an incision into the abdominal cavity, because they may be able to eliminate the need for making the incision. It should be noted that the ACS therapy system, as described herein, may be used for managing IAP due to any number of causes, including, for example, patients suffering blunt trauma, patients that have undergone surgery, and even non-surgical and non-trauma patients that develop IAH due to fluid loading for any number of reasons.

Figure 1:
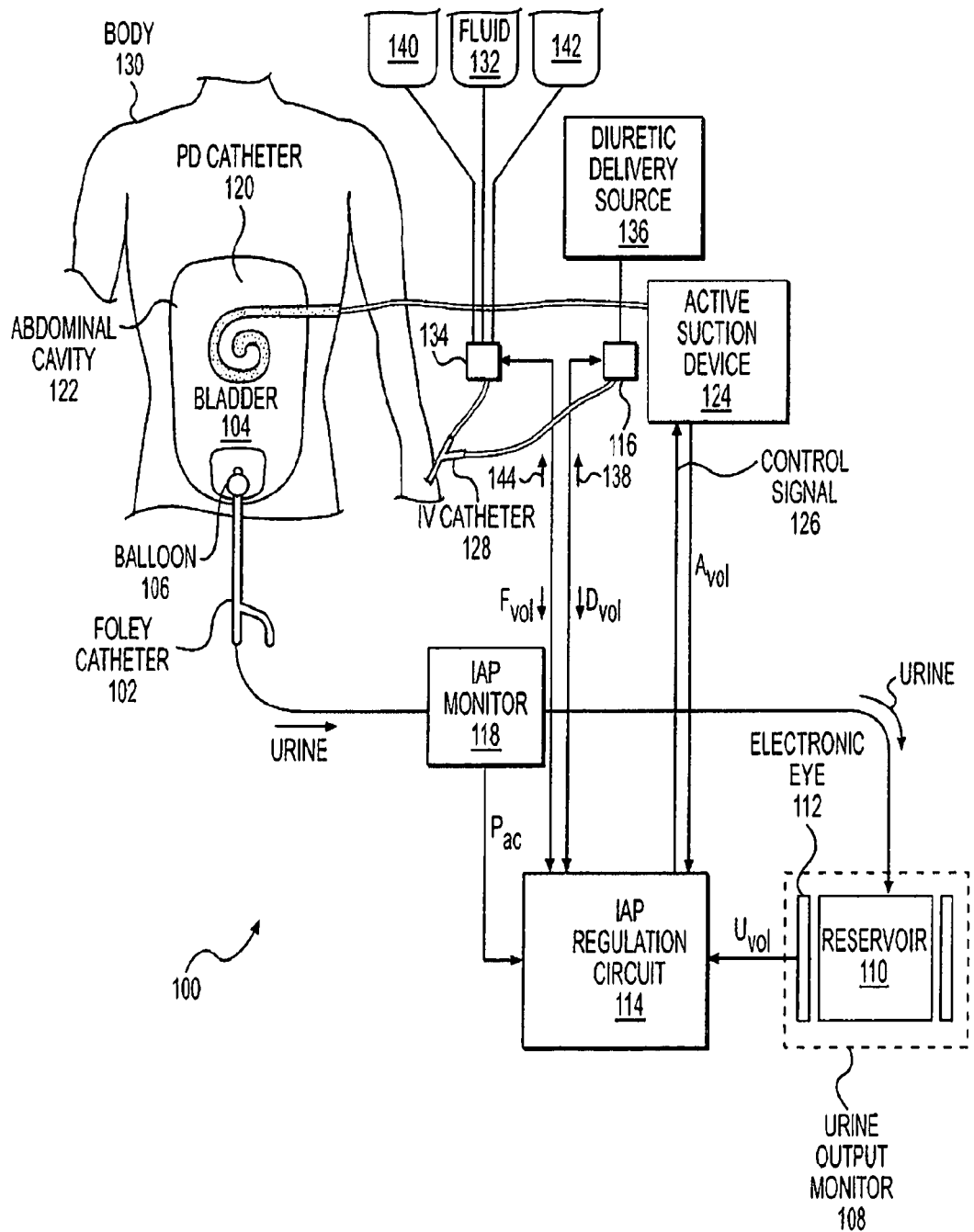
FIG. 1 illustrates an exemplary continuous and automated ACS therapy system.

FIG. 1 illustrates an exemplary automated ACS therapy system 100 according to one embodiment. In FIG. 1, a urine withdrawal device such as a Foley catheter 102 (a flexible plastic tube inserted into the bladder to provide continuous urinary drainage) may be used to withdraw urine from the bladder, although other methods of urine removal may be employed. The catheter 102 is inserted into the bladder 104 and a balloon 106 at the distal end of the catheter is inflated to secure the catheter within the bladder.

The ACS therapy system 100 may include a urine output monitor 108 that may receive urine through the catheter 102 and measure total urine output $U_{vol}$. The urine output monitor 108 may include a reservoir 110 for urine and an electronic "eye" 112 that senses the urine level to determine total urine output $U_{vol}$ on a real-time basis, either by continuously providing a total urine volume value or by providing a total urine volume value at periodic intervals. Either case is considered to be "continuous" monitoring as defined herein. One example of a urine output monitor is described in U.S. Pat. No. 4,343,316, which is incorporated by reference in its entirety in this application, and one example of a commercially available urine output monitor is the Bard CRITI-CORE® Monitor, although any means of continuously measuring time and urine output may be employed. The urine output monitor 108 optionally provides the $U_{vol}$ value to an IAP regulation circuit 114.

In addition, an Intra-Abdominal Pressure (IAP) monitor 118 is connected to the catheter 102, optionally through a drain line, to indirectly estimate the IAP by measuring the pressure within the bladder 104. The IAP monitor 118 is discussed in greater detail below. The IAP monitor 118 is operatively coupled to, and supplies a $P_{AC}$ value representative of the pressure in the abdominal cavity to the IAP regulation circuit 114, either by continuously providing a $P_{AC}$ value or by providing a $P_{AC}$ value at periodic intervals. Either case is considered to be "continuous" monitoring of the $P_{AC}$ value as defined herein.

An abdominal fluid removal device such as a Peritoneal Dialysis (PD) catheter 120 is used to withdraw fluid from the abdominal cavity 122, although other methods of fluid removal may be employed. The catheter 120 is inserted into the abdominal cavity 122 and may be connected to an active suction device 124, which may include a controllable pump and a reservoir for holding the withdrawn fluid. When activated, the active suction device 124 withdraws fluid from the abdominal cavity 122 through the catheter 120. The active suction device 124 may monitor and provide an abdominal fluid volume value $A_{vol}$ to the IAP regulation circuit 114, either by continuously providing a $A_{vol}$ value or by providing a $A_{vol}$ value at periodic intervals. Either case is considered to be "continuous" monitoring of the $A_{vol}$ value as defined herein.

An IntraVenous (IV) catheter 128 may optionally be used to administer fluid to the body 130, although other methods of fluid delivery may be employed. The catheter 128 is connected to a fluid delivery source 132 and is inserted into the body. When inserted, gravity or other means may be used to deliver fluids to the body. A fluid control and monitoring device 134 may optionally control and monitor the amount of fluid being delivered to the body, and may provide a fluid volume value $F_{vol}$ to the IAP regulation circuit 114, either by continuously providing a $F_{vol}$ value or by providing a $F_{vol}$ value at periodic intervals. Either case is considered to be "continuous" monitoring of the $F_{vol}$ value as defined herein.

The IV catheter 128 may optionally be used to administer diuretics to the body 130, although other methods of diuretic delivery may be employed. The catheter 128 may be connected to a diuretic delivery source 136. A diuretic control and monitoring device 116 may optionally control and monitor the amount of diuretics being delivered to the body, and may provide a diuretic volume value $D_{vol}$ to the IAP regulation circuit 114, either by continuously providing a $D_{vol}$ value or by providing a $D_{vol}$ value at periodic intervals. Either case is considered to be "continuous" monitoring of the $D_{vol}$ value as defined herein.

The ACS therapy system 100 according to embodiments described herein is an active feedback system. Based on one or more of the total urine output $U_{vol}$, the IAP value $P_{AC}$, the abdominal fluid volume value $A_{vol}$, the fluid volume value $F_{vol}$ and the diuretic volume value $D_{vol}$, the IAP regulation circuit 114 sends a control signal 126 that controls the active suction device 124. For example, if the IAP value $P_{AC}$ indicates that the intra-abdominal pressure is too great, the IAP regulation circuit 114 may cause the active suction device 124 to turn on and drain fluid from the abdominal cavity 122 through the catheter 120. In other words, the IAP regulation circuit 114 is operatively coupled to the catheter 120 to control the removal of abdominal fluid through the catheter 120. When the IAP value and/or the amount of fluid drained from the abdominal cavity reach certain levels as determined by the $A_{vol}$ value, or a certain amount of time has elapsed, the IAP regulation circuit 114 may cause the active suction device 124 to be turned off, causing the draining of fluid from the abdominal cavity to cease. Alternatively, after fluid has been drained from the abdominal cavity and the IAP value $P_{AC}$ has returned to acceptable levels, the IAP regulation circuit may send a control signal 138 to the diuretic control and monitoring device 116 to limit the amount of diuretics being administered to the patient. One skilled in the art will recognize that a number of different control operations may be possible utilizing the ACS therapy system 100 according to embodiments described herein.

Surrounding the urinary bladder 104 within the body 130 are a number of visceral organs. When pressure builds in the abdominal cavity 122 due to the buildup of fluids, the cavity expands and these organs push against the bladder 104. Therefore, the pressure in the bladder 104 is directly related to the IAP. The pressure within the bladder 104 can be monitored via the catheter 102 to indirectly measure the amount of IAP present. As mentioned above, an IAP monitor 118 may be connected to the catheter 102 to indirectly estimate the IAP by measuring the pressure within the bladder.

There are a number of methods available to indirectly measure the IAP through the catheter 102 in a manner suitable for use in an ACS therapy system. For example, an IAP monitor 118 may be used to automatically provide real-time readings of IAP levels without the injection of fluid directly into the bladder itself. Examples of such an IAP monitor are described in International Patent Application No. PCT/US06/27264, entitled "Intra-Abdominal Pressure Monitoring System" and filed Jul. 13, 2006, which is incorporated by reference in its entirety in this application and attached hereto, wherein the balloon of a Foley catheter inflated within the bladder or a separate balloon may be used to determine the pressure within the bladder and provide an estimate of the IAP, without the need to inject fluid directly into the bladder.

Figure 2:
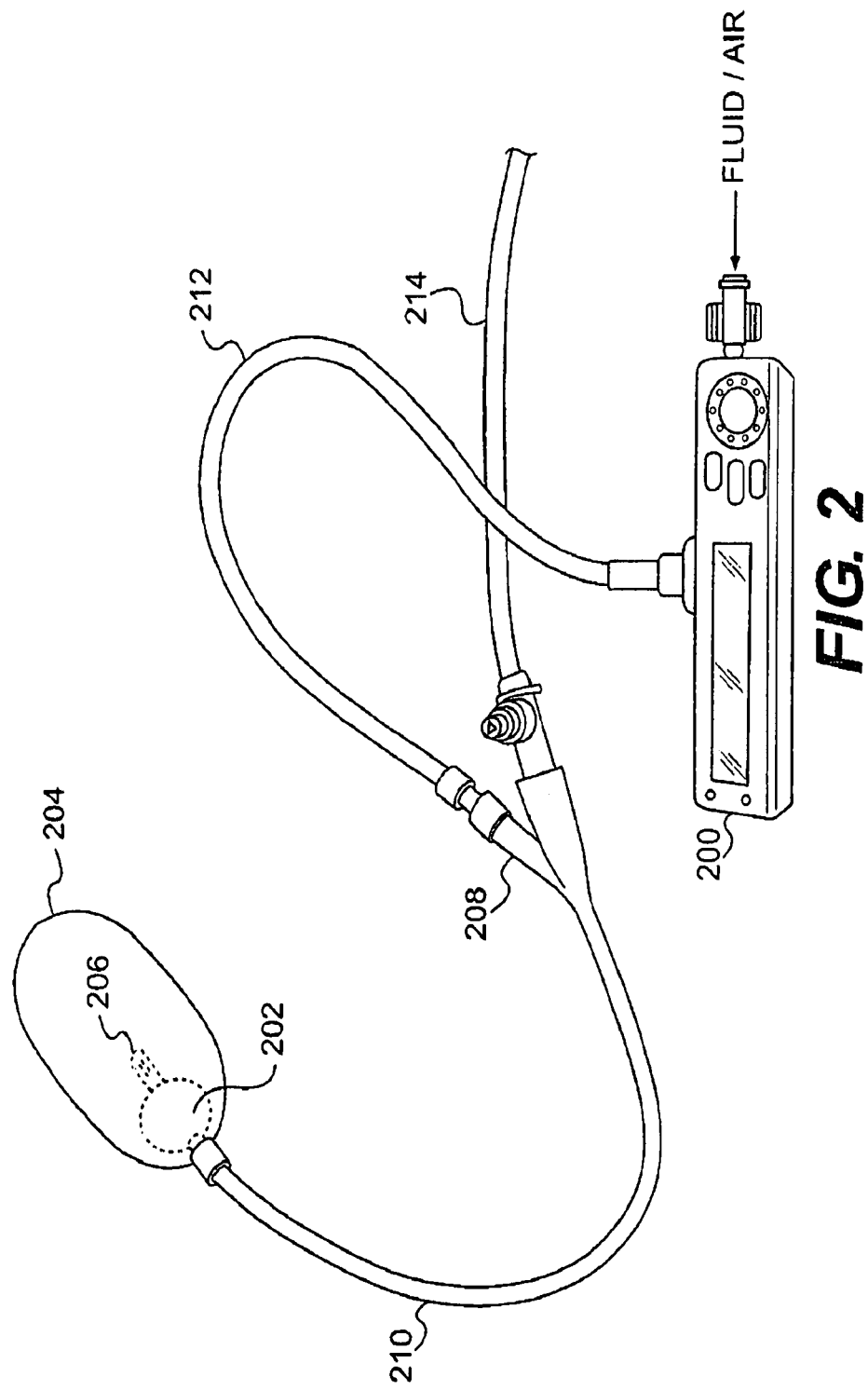
FIG. 2 is an illustration of an exemplary IAP monitor and Foley catheter.

FIG. 2 is an illustration of an exemplary IAP monitor 200 and Foley catheter 210 for use in an ACS therapy system. In FIG. 2, an inflatable element 202 is expanded inside a patient's bladder 204 to monitor IAP. In this illustration, an appropriately sized/shaped inflatable element (e.g., balloon) 202 mounted on a catheter shaft 206 is expanded inside the bladder 204 of a patient using fluid or air. The resistance felt by the balloon 202 when making contact with the bladder wall is detected through an inflation lumen via a pressure transducer or sensor, which in one embodiment may be located within the IAP monitor 200 (as in FIG. 2). The specific design of the inflatable element 202 can take on various shapes and/or sizes, such as spherical, multi-lobed, oval, longitudinal, etc. Further, the inflatable element 202 can also serve as an anchor to prevent slippage of the catheter 210 out of the patient's bladder 204 (which is the standard function of an inflatable element on the end of a Foley catheter), although this anchor function may also be performed by a separate element.

In FIG. 2, the inflatable element 202 has been expanded inside of the bladder 204 to illustrate the functioning of the system. In this particular illustration, the IAP monitor 200, which may include a fluid/air compensation chamber and pressure sensor, is attached via tubing 212 to the inflation port 208 and connected to an inflation lumen. The pressure sensor may be wired to a readout (e.g., display, memory, etc.) or it may be wirelessly connected. In general, a pressure sensor may transmit information (e.g., IAP measurement $P_{AC}$) to an IAP regulation circuit. The inflation port 208 has an inflation valve as known to one skilled in the art. The fluid/air compensation chamber may be located within the IAP monitor 200 (as in FIG. 2) or may be stand-alone, and includes a miniature pump with programmable controls, an embedded circuit to program and control the parameters of operations such as inflation time, sensing time, frequency of on-off cycle, etc., and a fluid/air reservoir. The fluid/air compensation chamber compensates for any fluid/air diffusion through the balloon 202, ensuring a steady baseline. The pump may be battery operated. In the illustration shown, the drainage and sensing functions are de-coupled, meaning that urine output rate can be independently monitored. Because the sensing element cannot be inflated continuously without compromising the bladder volume, discrete measurements will be generated automatically, as programmed by monitoring needs under control of the IAP regulation circuit. The inflatable element 202 at the distal end of the catheter 210 is shown inflated and substantially in contact with the bladder 204, providing pressure readings to the pressure sensor. As mentioned, the pressure measurement(s) occur in this illustration simultaneously with the drainage of urine from the bladder 204 as the urinary lumen of the catheter 210 remains open and in fluid communication with an attached drain tube 214. The proximal end of the catheter is attached to a proximal connection member as described above such that sampling of urine may also be performed simultaneously with the pressure reading(s).

Figure 3:
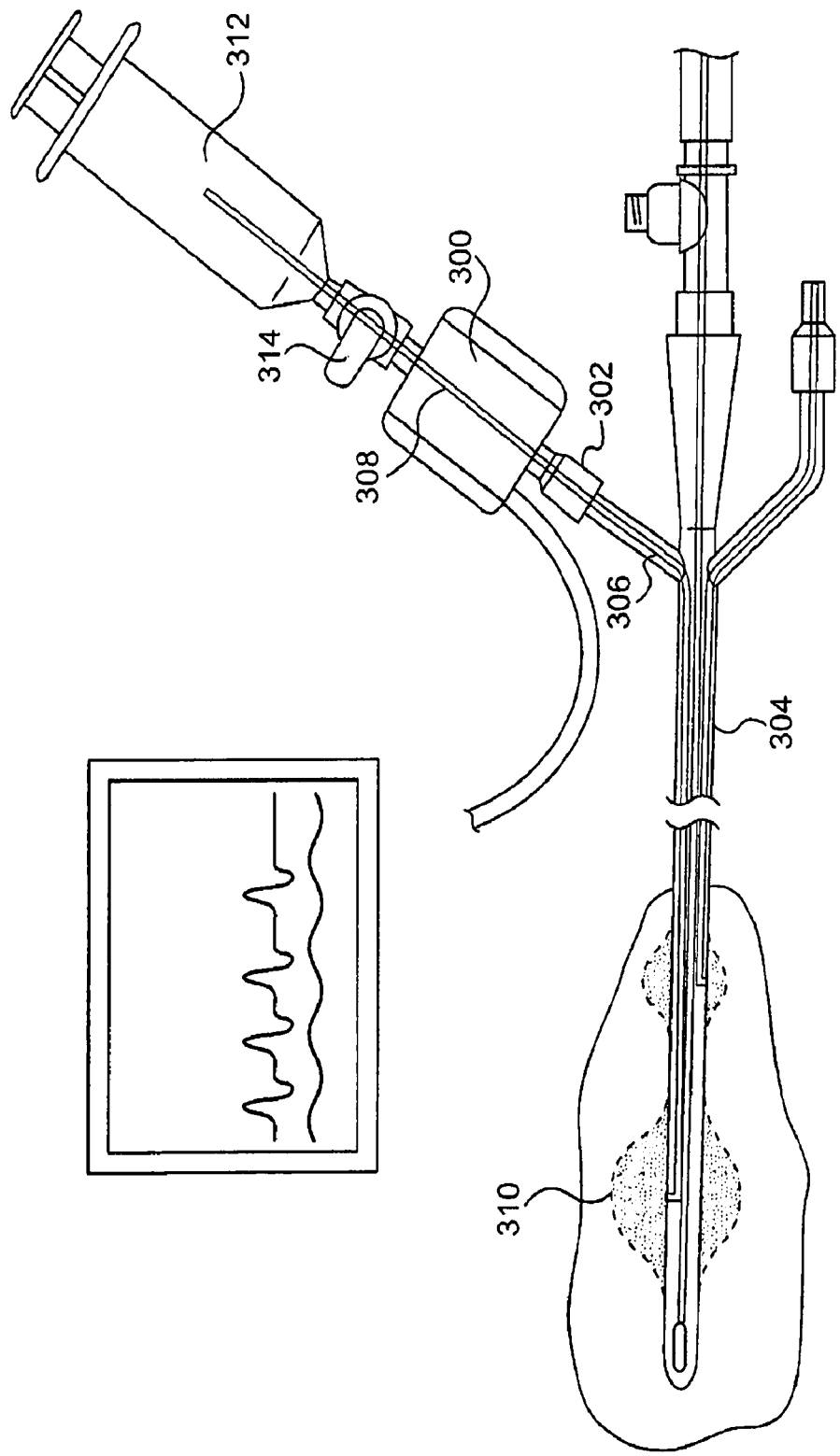
FIG. 3 is an illustration of another exemplary IAP monitor and Foley catheter.

FIG. 3 is an illustration of another exemplary IAP monitor 300 and Foley catheter 304. In FIG. 3, the port 302 used to measure pressure is a second fluid lumen 306 of a 3-way Foley catheter 304. In this embodiment, fluid or air is injected through a bypass lumen 308 that is connected to the second fluid lumen 306 via an entry port 302. The fluid/air fills and inflates a second bulb 310. Fluid/air is provided by a fluid infuser 312 and pressure is measured by an in-line pressure transducer or IAP monitor 300 under control of an IAP regulation circuit. After inflation of the second bulb 310, a valve 314 controllable by the IAP regulation circuit may be used to prevent backflow from the bulb, and pressure may be measured reflecting IAP. The fluid/air may be removed by opening the valve 314 and withdrawing the fluid using the fluid infuser 312 (shown here as a syringe), both under control of the IAP regulation circuit. It should be understood that either of the IAP monitors illustrated in FIGS. 2 and 3 may be controllable by IAP regulation circuit 114 of FIG. 1 to inflate the sensing element and thereafter take continuous measurements of IAP.

As mentioned above, an abdominal fluid removal device is used to withdraw fluid from the abdominal cavity. One example of an abdominal fluid removal device is a Peritoneal Dialysis (PD) catheter. Referring again to FIG. 1, which illustrates a PD catheter 120, the PD catheter is a length of tubing with holes in its sides that is placed within the abdominal cavity through a small incision. In its normal use for dialysis, the PD catheter 120 is used to inject a cleansing dialysis solution into the abdominal cavity. The solution pulls extra fluid and waste products from the body through the peritoneum, which is a membrane lining the abdominal cavity. When the dialysis solution is subsequently withdrawn from the abdominal cavity through the tubing, the extra fluid and waste products are removed as well. The PD catheter may also be used not for injecting fluid, but only to pull excess fluid from the abdominal cavity when the active suction device 124 is activated.

Figure 4:
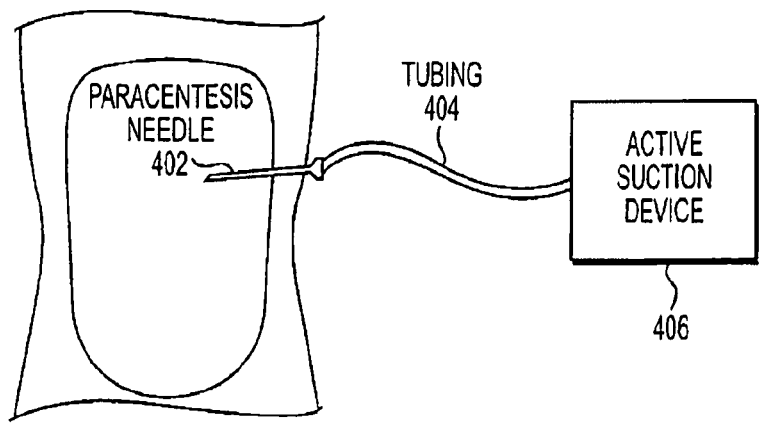
FIG. 4 is an illustration of the use of a paracentesis needle to extract fluid from the abdominal cavity.

It is noted that the PD catheter is just one example of how fluid in the abdominal cavity can be removed. Paracentesis is another method of removing fluid from the abdominal cavity. FIG. 4 is an illustration of the use of a paracentesis needle 402 to extract fluid from the abdominal cavity. Initially, the paracentesis needle 402, which is connected to the distal end of tubing 404, is inserted through the abdominal wall. The tubing 404 is connected at its proximal end to an active suction device 406. When an IAP regulation circuit determines that fluid should be removed from the abdominal cavity to relieve the IAP, the active suction device 406 is activated and fluid is removed through the paracentesis needle 402.

Figure 5A:
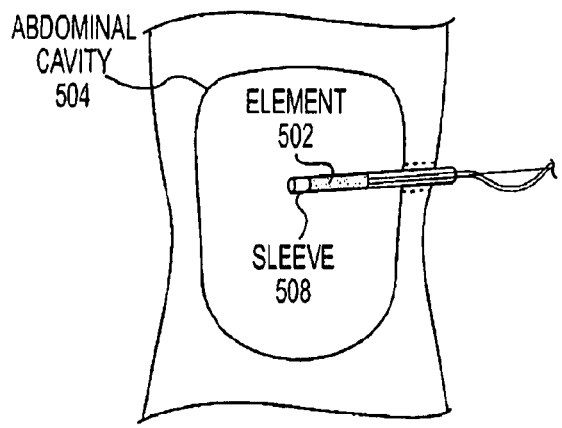
FIG. 5a illustrates a large surface area abdominal cavity fluid removal element within a sleeve for insertion into the abdominal cavity.
Figure 5B:
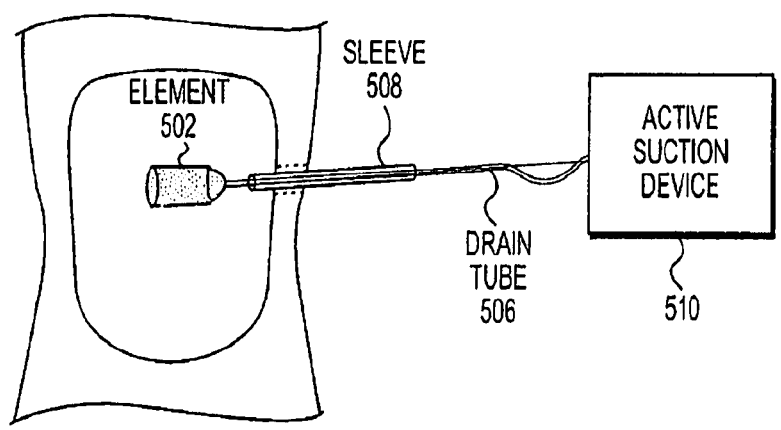
FIG. 5b illustrates a large surface area abdominal cavity fluid removal element removed from the sleeve and deployed in the abdominal cavity.

Other fluid removal devices such as large surface area elements (e.g. sponges or membranes) through which fluid is withdrawn by negative pressure or osmosis may also be used. An example of such a negative pressure sponge is the KCI® Vacuum Assisted Closure (V.A.C.®) ATS® system described at www.kcil.com, the contents of which are incorporated by reference in their entirety in this application. FIG. 5a illustrates a large surface area abdominal cavity fluid removal element 502. In FIG. 5a, an element such as a sponge or membrane 502 through which fluid may be drawn is placed within the abdominal cavity 504. To minimize the incision needed to pass such an element 502 into the abdominal cavity 504, the element may be initially compressed into a small diameter and passed through the incision. In the example of FIG. 5a, the element 502 is compressed inside a sleeve 508 during insertion. As shown in FIG. 5b, once inside the abdominal cavity, the sleeve 508 is pulled back to enable the element 502 to be fanned out or expanded to restore the large surface area. A drain tube 506 may be connected to the element 502 and the active suction device 510. When the active suction device 510 is activated, fluid is removed from the abdominal cavity through the element 502 and catheter 506. Prior to removing the element 502, the sleeve 508 is pushed over the element, compressing it for removal through the incision.

Referring again to FIG. 1, the fluid delivery source 132 provides fluids to the body through catheter 128. However, the ACS therapy system 100 may also utilize the feedback received by the IAP regulation circuit 114 to determine whether a different type of IV fluid (e.g. different fluid resuscitation protocols 140, 142) should be delivered to the body through the catheter 128. The different types of IV fluids that may be used include, but are not limited to, Racemic Lactated Ringers, L-Lactated Ringers, Ketone Ringers, Pyruvate Ringers, Hetasatrch, and Hypertonic Saline. For example, if the IAP regulation circuit 114 determines indicates that a large amount of fluid is being removed from the abdominal cavity, or that some other complication capable of being detected by the parameters monitored by the IAP regulation circuit 114 is occurring, it may provide an visual or audio indication that a different type of IV fluid should be used, or the IV fluid should be applied at a slower rate. Alternatively, the IAP regulation circuit 114 may provide a control signal 144 to a fluid switch (which may optionally be located within the fluid control and monitoring device 134) to automatically change fluids or rates of delivery.

Figure 6:
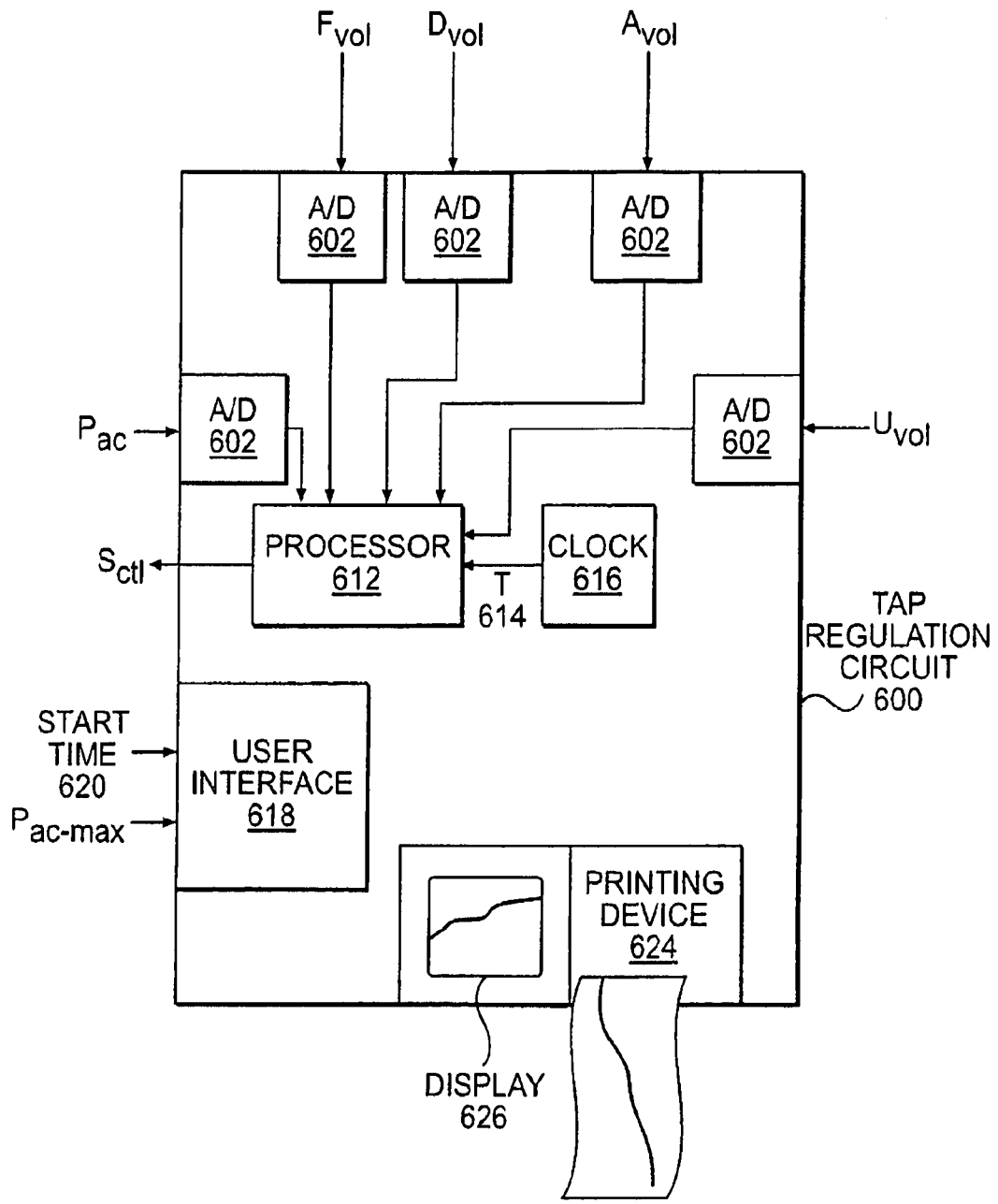
FIG. 6 is an illustration of an exemplary IAP regulation circuit.

FIG. 6 is an illustration of an exemplary IAP regulation circuit 600 which may include A/D converters 602 for receiving one or more of a urine volume value $U_{vol}$, a IAP value $P_{AC}$, an abdominal cavity fluid output value $A_{vol}$, a diuretic volume value $D_{vol}$, and a fluid volume value $F_{vol}$, if those signals are in analog form. The digitized values for one or more of these parameters may be transmitted to a processor 612 along with an elapsed time signal 614 from a clock circuit 616. The IAP regulation circuit 600 may include a user interface 618 for enabling a user to establish a start time 620 so that total elapsed time 614 can be determined, and for enabling the user to input various other parameters, such as a threshold IAP value $P_{AC\_}$max above which the processor 612 may automatically direct an active suction device to withdraw fluid from the abdominal cavity. The user interface 618 may also enable the user to program the IAP regulation circuit 600 to manage ACS. In a simple example, the user may input $P_{AC\_}$max, and program the processor 612 to automatically send a suction control signal $S_{ctl}$ to an active suction device when the IAP value $P_{AC}$ is greater than or equal to $P_{AC\_}$max. In other words, the algorithm executed by the processor may read: "if $P_{AC} \geq P_{AC\_}$max, then $S_{ctl}$=asserted". In another example, the user may input a periodic time interval and program the processor to control an IAP monitor to take an IAP reading every periodic time interval. One skilled in the art will appreciate that there are a number of algorithms that may be implemented by the IAP regulation circuit to monitor IAP, the fluid and the diuretics being administered, and control the withdrawal of fluid from the abdominal cavity, or control the amount or type of fluid or diuretics being administered.

The IAP regulation circuit 600 may also include a continuous printing device 624 or graphical display 626 and memory for printing out and/or displaying and storing any one or more of the parameters being monitored and computed on a continuous basis to show one or more of the changes in IAP, urine output, abdominal fluid removal, fluid and diuretics being administered, and the relationship between them, over time. The display or printout may provide continuous (connected) graphs of the parameters, or may provide data points at periodic intervals. Either case is considered to be "continuous" displaying or printing as defined herein.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. An Abdominal Compartment Syndrome (ACS) therapy system, comprising:
    an Intra-Abdominal Pressure (IAP) monitor configured to measure and provide an indication of IAP;
    a urine withdrawal device coupled to the IAP monitor and configured to drain urine from the patient, the IAP monitor configured to measure the indication of IAP by measuring bladder pressure through the urine withdrawal device;
    an abdominal fluid removal device configured to remove fluid from an abdominal cavity of a patient; and
    an IAP regulation circuit operatively coupled to the IAP monitor and the abdominal fluid removal device and configured to receive the indication of IAP from the IAP monitor and automatically control the removal of fluid from the abdominal cavity through the abdominal fluid removal device based on the indication of IAP.

2. The ACS therapy system according to claim 1, further comprising an active suction device coupled to the abdominal fluid removal device and the IAP regulation circuit and configured to withdraw fluid from the abdominal cavity through the abdominal fluid removal device under control of the IAP regulation circuit.

3. The ACS therapy system according to claim 2, the active suction device configured to provide an indication of a total abdominal fluid volume being drained from the abdominal cavity to the IAP regulation circuit.

4. The ACS therapy system according to claim 3, the IAP regulation circuit comprising a processor configured to receive the indication of IAP and send a first control signal to the active suction device to withdraw fluid from the abdominal cavity through the abdominal fluid removal device when the indication of IAP meets or exceeds a first predetermined threshold.

5. The ACS therapy system according to claim 4, the processor configured to send a second control signal to the active suction device to cease withdrawing fluid from the abdominal cavity through the abdominal fluid removal device when the indication of the total abdominal fluid volume being drained meets or exceeds a predetermined threshold.

6. The ACS therapy system according to claim 4, the processor configured to send a second control signal to the active suction device to cease withdrawing fluid from the abdominal cavity through the abdominal fluid removal device when a predetermined amount of time has elapsed.

7. The ACS therapy system according to claim 1, further comprising:
    a fluid delivery source for providing fluid to the patient; and
    a fluid control and monitoring device coupled to the fluid delivery source and the IAP regulation circuit and configured to control and monitor an amount of fluid being administered to the patient, and provide an indication of the amount of fluid being administered to the patient to the IAP regulation circuit.

8. The ACS therapy system according to claim 7, further comprising an IV catheter coupled to the fluid delivery source and configured to administer fluid to the patient.

9. The ACS therapy system according to claim 7, the fluid control and monitoring device configured to switch between multiple fluid delivery sources, and the IAP regulation circuit configured to programmably control the fluid control and monitoring device to switch between the multiple fluid delivery sources in accordance with monitored values received by the IAP regulation circuit.

10. The ACS therapy system according to claim 1, further comprising a urine output monitor coupled to mine urine withdrawal device and configured to measure and provide an indication of a total urine volume being drained from the patient.

11. The ACS therapy system to claim 10, the urine output monitor configured to provide the indication of the total urine volume being drained from the patient to the IAP regulation circuit.

12. The ACS therapy system according to claim 1, further comprising:
    a diuretic delivery source configured to provide a diuretic to the patient; and
    a diuretic control and monitoring device coupled to the diuretic delivery source and the IAP regulation circuit and configured to control and monitor an amount of regulation diuretic being administered to the patient, and provide an indication of the amount of diuretic being administered to the patient to the IAP regulation circuit.

13. The ACS therapy system according to claim 12, further comprising an IV catheter coupled to the diuretic delivery source and configured to administer the diuretic to the patient.

14. The ACS therapy system according to claim 1, the abdominal fluid removal device comprising a Peritoneal Dialysis (PD) catheter, a paracentesis needle, or a large surface area abdominal cavity fluid removal element.

15. The ACS therapy system according to claim 1 the urine withdrawal device including a balloon for inflation in a bladder, the IAP monitor coupled to an inflation device and the balloon through an inflation lumen for inflating the balloon, and the IAP monitor comprising a pressure sensor configured to sense pressure felt by the inflated balloon within the bladder.

16. The ACS therapy system according to claim 1, the IAP regulation circuit comprising a display device configured to continuously display the IAP.

17. The ACS therapy system according to claim 1, the IAP regulation circuit comprising a user interface configured to enable a user to input a threshold IAP value.

18. The ACS therapy system according to claim 1, the IAP regulation circuit comprising a user interface configured to enable a user to program the IAP regulation circuit to control the removal of fluid from the abdominal cavity.

19. An Abdominal Compartment Syndrome (ACS) therapy system, comprising:
   an Intra-Abdominal Pressure (IAP) monitor configured to measure and provide an indication of IAP;
   an abdominal fluid removal device configured to remove fluid from an abdominal cavity of a patient; an IAP regulation circuit operatively coupled to the IAP monitor and the abdominal fluid removal device and configured to receive the indication of IAP from the IAP monitor and control the removal of fluid from the abdominal cavity through the abdominal fluid removal device;
   a urine withdrawal device coupled to the IAP monitor and configured to drain urine from the patient;
   a urine output monitor coupled to the urine withdrawal device and configured to measure and provide an indication of a total urine volume being drained from the patient;
   an active suction device coupled to the abdominal fluid removal device and the IAP regulation circuit and configured to withdraw fluid from the abdominal cavity through the abdominal fluid removal device under control of the IAP regulation circuit;
   a fluid delivery source configured to provide fluid to the patient; and
   a diuretic delivery source configured to provide a diuretic to the patient.

20. The ACS therapy system according to claim 19, wherein the fluid delivery source is configured to provide fluid to the patient intravenously.

* * * * *